United States Patent [19]

Quallich

[11] Patent Number: 5,608,071

[45] Date of Patent: Mar. 4, 1997

[54] SYNTHESIS OF 3-BROMO-5-CHLORO-2-ALKYL-PYRIDINE DERIVATIVES

[75] Inventor: George J. Quallich, North Stonington, Conn.

[73] Assignee: Pfizer Inc., New York, N.Y.

[21] Appl. No.: 429,408

[22] Filed: Apr. 26, 1995

Related U.S. Application Data

[60] Division of Ser. No. 215,071, Mar. 18, 1994, Pat. No. 5,436,344, which is a continuation-in-part of Ser. No. 619,850, Nov. 29, 1990, abandoned.

[51] Int. Cl.$^6$ ............... C07D 213/87; C07D 213/79; C07D 213/61
[52] U.S. Cl. ............................ 546/345; 546/339
[58] Field of Search ...................... 548/178, 268; 546/345, 339

[56] References Cited

U.S. PATENT DOCUMENTS

| | | | |
|---|---|---|---|
| Re. 28,532 | 8/1975 | Carlson et al. | 546/341 X |
| 2,754,301 | 7/1956 | Cislak | 546/344 |
| 2,789,982 | 4/1957 | Cislak | 546/344 |
| 3,004,957 | 10/1961 | Lynn | 546/341 X |
| 3,400,126 | 9/1968 | Brust et al. | 546/344 |
| 3,535,328 | 10/1970 | Zielinski | 546/341 X |
| 3,637,714 | 1/1972 | Carlsson et al. | 546/341 X |
| 3,737,542 | 6/1973 | Carlsson et al. | 546/341 X |
| 4,457,934 | 7/1984 | Wong | 546/341 X |
| 4,579,850 | 4/1986 | Wong | 546/341 X |
| 4,745,193 | 5/1988 | Howarth et al. | 546/345 |
| 4,931,452 | 6/1990 | Malhotra et al. | 514/344 |
| 5,436,344 | 7/1995 | Quallich | 546/268 |

FOREIGN PATENT DOCUMENTS 56-115776  9/1981  Japan .................... 546/345

OTHER PUBLICATIONS

Ishihara II, Chemical Abstracts, vol. 95, #203765n(1981).

*Primary Examiner*—Floyd D. Higel
*Attorney, Agent, or Firm*—Peter C. Richardson; Paul H. Ginsburg; Grover F. Fuller, Jr.

[57] ABSTRACT

Compounds of the formula

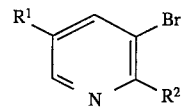

I which are intermediates in the preparation of hydantoin aldose reductase inhibitors and methods of preparing these intermediates.

3 Claims, No Drawings

SYNTHESIS OF 3-BROMO-5-CHLORO-2-ALKYL-PYRIDINE DERIVATIVES

This is a division of Ser. No. 08/215,071, filed Mar. 18, 1994, which issued as U.S. Pat. No. 5,436,344 on Jul. 25, 1995, which in turn is a continuation-in-part of application Ser. No. 07/619,850, filed Nov. 29, 1990, now abandoned.

FIELD OF THE INVENTION

The present invention relates to azatetralone compounds which are intermediates in the preparation of hydantoin aldose reductase inhibitors and methods of preparing these intermediates.

BACKGROUND OF THE INVENTION

European Patent Application No. 88307985.7 discloses azolidinedione derivatives useful as hydantoin aldose reductase inhibitors. These compounds are useful in the treatment of certain chronic complications arising from diabetes mellitus, such as cataracts, retinopathy and neuropathy. European Patent Application No. 85307712.1 discloses the preparation of these compounds via dichloromalonoaldehyde intermediates. The alternative synthesis of the present invention is advantageous because it avoids the use of dichloromalonoaldehyde which is a known mutagen. The present synthesis also produces azatetralones in a chiral form.

Carbon—carbon bond formation by cross coupling of Grignard reagents with organic halides mediated by catalysts such as 1,2-bis(diphenylphosphino)ethane nickel (II) (dppe) and 1,3-bis(diphenylphosphino)propane nickel (II) chloride (dppp) has been shown in a variety of systems including arenes, furans, thiophenes, pyridines, and quinolines. (K. Tamao, et al., *Tetrathedron*, 38, No. 22, pp. 3347–3354 (1982)). While single and double displacements of aromatic halogens with Grignard reagents and the aforementioned nickel/phosphine ligands has been shown, regiospecific displacement of one halogen in a polyhalogenated aromatic ring system had not been accomplished.

Ring systems have also been assembled, by so-called Parham cyclization involving low temperature transmetallation of a halogen, often bromine, with n- or t-butyllithium and subsequent intramolecular cyclization (Parham, W. E. et al., 40 J.O.C. 2394 (1975); Parham. W. E. et ed., *Acc. Chem., Res.*, 15, 300 (1975); and Snieckus, V. et al., *Tett. Lett.* 2933 (1987)). The electrophiles in this approach have included carboxylic acids, halogens, epoxides, and Schiff bases.

SUMMARY OF THE INVENTION

The present invention relates to compounds of the formula

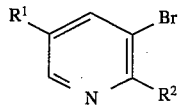   I wherein $R^1$ is hydrogen, fluoro, chloro, bromo, nitro, trifluoromethyl, $C_1$ to $C_4$ alkoxy, $C_1$ to $C_4$ alkylthio or $C_1$ to $C_6$ alkyl and $R^2$ is bromo, iodo or a group of the formula

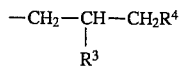

wherein $R^3$ is hydrogen or $C_1$ to $C_6$ alkyl, $R^4$ is —CH=$CH_2$, —$CH_2$—$YR^5$, or —$COR^6$, $R^5$ is hydrogen or an acid labile alcohol protecting group (e.g., tetrahydropyranyl ether and t-butyldimethylsilyl ether), Y is oxygen or sulfur, and $R^6$ is —$NR^7R^8$ or —$OR^9$ wherein $R^7$, $R^8$ and $R^9$ are independently selected from hydrogen or $C_1$ to $C_6$ alkyl, or the alkaline and alkaline earth metal salts thereof.

The present invention also relates to a method of preparing a compound of formula I wherein R2 is

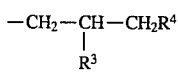

as is defined for formula I comprising performing a regiospecific displacement of a halo-substituent at the 2 position of a compound of formula I in which $R^2$ is bromo or iodo by reacting said compound of formula I wherein $R^2$ is bromo or iodo with Grignard reagent of the formula

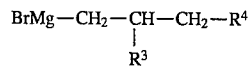   IV wherein in $R^3$ is as defined for formula I and $R^4$ is —CH=$CH_2$ or —$CH_2$—$YR^5$, Y is O, and $R^5$ is an acid labile alcohol protecting group in the presence of a phosphine ligand catalyst and at a sufficiently low temperature such that a regiospecific displacement of only the $R^2$ substituent occurs.

The present invention also relates to performing Parham cycliacylation by reacting a compound of formula I wherein $R^2$ is

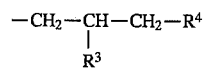

$R^4$ is —$COR^6$, $R^6$ is —$NR^7R^8$ or —$OR^9$, $R^9$ is hydrogen, and $R^3$, $R^7$, and $R^8$ are as defined for formula I with an alkyl lithium compound so as to form the corresponding azatetralone.

DETAILED DESCRIPTION OF THE INVENTION

The following reaction scheme illustrates the preparation of the compounds of the present invention and the processes of the present invention.

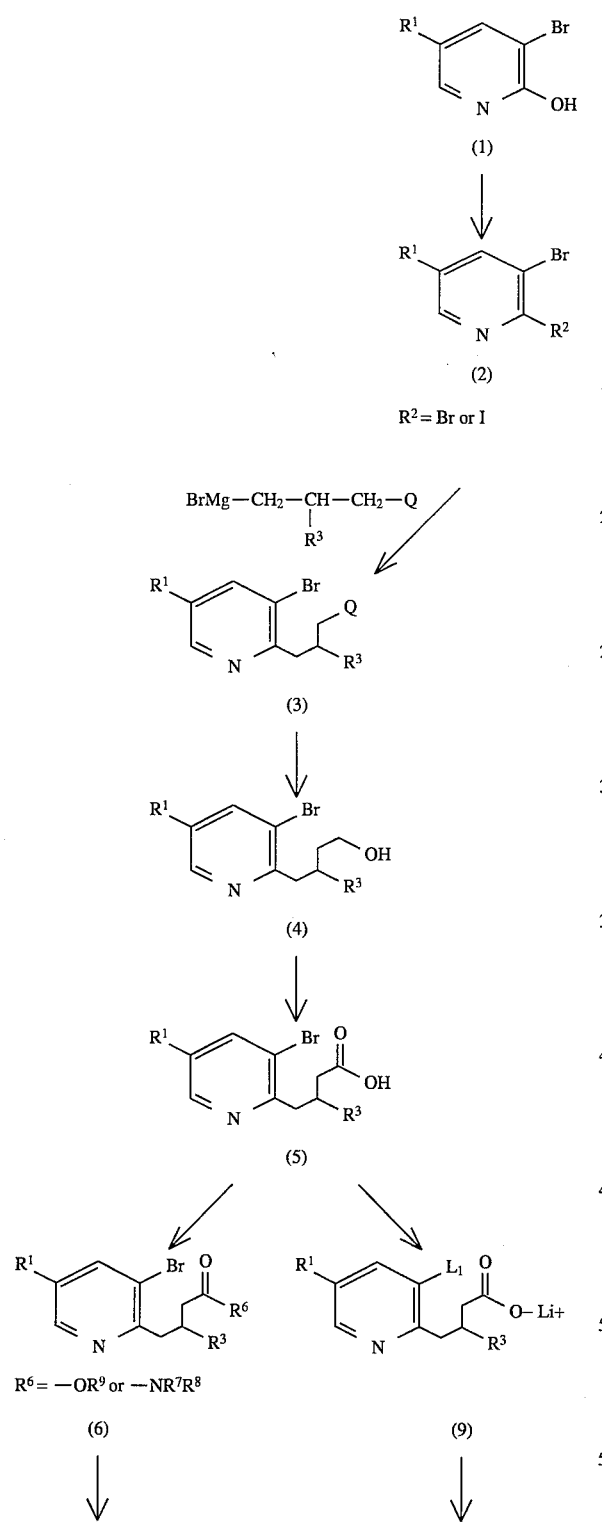
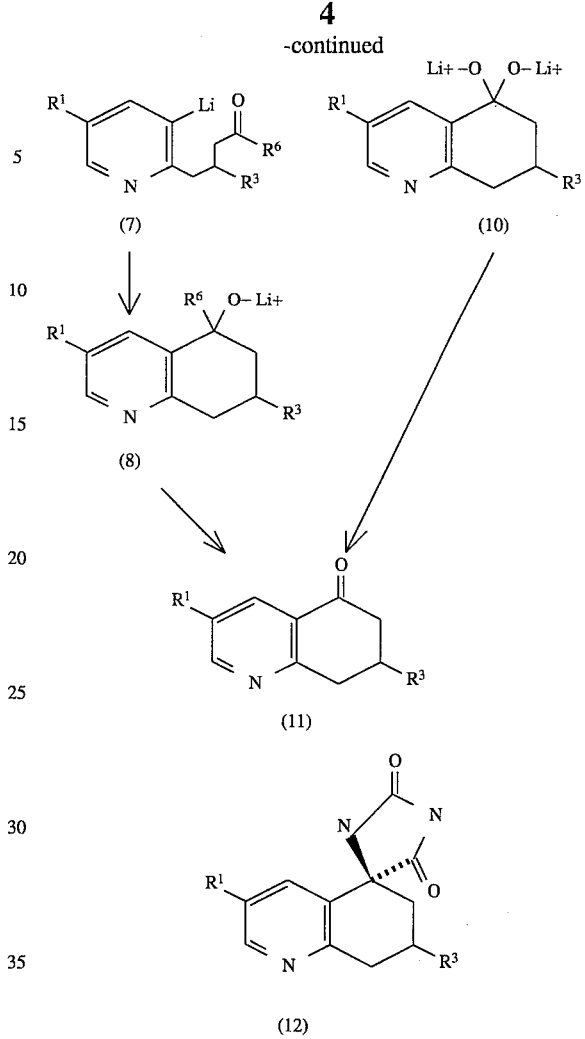

The 3-bromo, 2-hydroxy substitute pyridine (1) is formed by reacting a 3-bromo, 2-amino substituted pyridine with water in the presense of a suitable diazotizing reagent to produce the corresponding 3-bromo, 2-hydroxy form (1). Suitable diazotizing reagents include t-butyl nitrite, sulfuric acid/sodium nitrite, and hydrochloric acid/sodium nitrite, preferably the latter of the three. The reaction is carried out at between −10 and 50° C., preferably 0° C.

The pyridine (1) is then converted to the corresponding di-halo-substituted form (2) via nucleophilic displacement by heating (1) to between 80° and 120° C. in a polar aprotic solvent such as 1,3-dimethyl-2-imidazolidone or dimethylformamide. A halo-containing nucleophilic reagent such as phosphorous oxybromide or a solution of 1:1/triphenylphosphine:bromine is used to effect displacement of the hydroxy group.

The regiospecific displacement of the halo-substituent at the 2 position of the pyridine (2) is carded out with a Grignard reagent under the reaction conditions of a sufficiently low temperature such that the displacement of only the $R^2$ substituent occurs. The displacement reaction is preferably run at between about −20° and about 15° C. and generally takes from between about 30 minutes to about 4 hours for all the reacting compounds to be used, the time depending on the severity of the reaction conditions. The displacement takes place in the presence of a phosphine ligand catalyst such as the aforementioned dppe or dppp catalysts, preferably dppp, the catalysts being present at a concentration of approximately 0.1 equivalents.

Q is an acid labile alcohol protecting group and can be either —CH=CH$_2$ or —CH$_2$—OP where P is an acid labile alcohol protecting substituent and can be, for example, tetrahydropyranyl, methoxymethyl, t-butoxymethyl, 2-methoxyethoxymethyl, 2-(trimethylsilyl)ethoxymethyl, tetrahydropyranyl, 4-methoxytetrahydropyranyl, tetrahydrofuranyl, 1-ethoxyethyl, 1-methyl-1-methoxyethyl, 1-(isopropoxy)ethyl, t-butyl, benzyl, triphenylphenytmethyl, t-butyldimethylsilyl, and t-butyldiphenylsilyl. Once the carbon atoms necessary to construct the azatetralone (11) have been assembled, pyridine (3) is converted to the carboxylic acid (5) by one of several methods depending on Q. Where Q is —CH$_2$—OP, the protecting substituent can be hydrolyzed to form the corresponding hydroxy-alkyl substituted form (4) with various acid reagents such as pyridium tosylate in ethanol at a temperature of from ambient temperature (i.e. about 30° C.) to about 100° C., preferably approximately 55° C.

The hydroxyalkyl substituted benzene (4) is then converted to the corresponding acid (5) using an oxidation reagent, such as Jones reagent [Fieser & Fieser Vol. 1 p. 142 (1967)] or pyridium dichromate, preferably Jones reagent. The reaction can be run at between about 0° and about 35° C.

Where Q is —CH=CH$_2$, pyridine (3) is converted to the carboxylic acid (5) by one of two methods of oxidative cleavage. The first is a two-step process involving treating the pyridine (3) with the oxidative reagent ozone in the presence of a polar solvent such as methylene chloride or methanol with carbon tetrachloride. This reaction is run at a temperature of between about −78° and about 0° C. After the first step, the resulting product is then treated with either sodium chlorite or Jones reagent to produce the carboxylic acid (5). The reaction with sodium chlorite should be carded out in water at a temperature of between about −20° and about 20° C. The reaction with Jones reagent should be carded out in a polar solvent such as acetone at a temperature of between about 0° and 30° C.

The second oxidative cleavage method of converting the pyridine (3) where Q is —CH=CH$_2$ is by using an oxidizing reagent such as permangenate or ruthenium tetroxide which, in one step, converts it directly to the carboxylic acid (5). This reaction takes place at a temperature of between about 0° C. and ambient temperature (about 30° C.). The reaction solvents are as follows: carbon tetrachloride, acetonile, and water (ratio of about 2:2:3, respectively) for ruthenium tetroxide; and acetone for permangenate.

The acid (5) can also be converted to a base salt thereof. This is accomplished by treating the acid (5) with alkaline or alkaline earth metal hydroxide type bases. These bases include sodium hydroxide, potassium hydroxide, and lithium hydroxide.

Prior to Parham cycliacylation, however, the cycliacylation process can be enhanced by converting the acid (5) to the corresponding amide (6) where $R^6$ is $NR^7R^8$. This is accomplished by treating the acid with an amide-forming reagent and an amine $HNR^7R^8$. Amide-forming reagents include (2-ethoxy-1-ethyoxycarbonyl-1,2-dihydroquinoline) [EEDQ] or an alkyl carbodiimide compound, preferably a dimethyl carbodiimide such as 1-(3-dimethylpropyl)-3-ethylcarbodiimide hydrochloride. The reaction should take place in a polar solvent, preferably methylene chloride. The reaction temperature should be between about 0° C. and ambient temperature (about 30° C.).

The acid (5) can also be converted to the corresponding ester (6) where $R^6$ is —$OR^9$. The ester (6) is formed by reacting the acid (5) with the alcohol $R^9OH$ in the presence of an ester-forming reagent such as a mineral acid or an alkyl carbodiimide. Suitable alkyl carbodiimide include a dimethyl carbodiimide such as 1-(3-dimethylpropyl)-3-ehtylcarbodiimide hydrochloride. Acceptable mineral acids include hydrochloric acid or sulfuric acid, preferably hydrochloric acid. The reaction is run at a temperature between 0° C. and ambient temperature (about 30° C.).

Either the acid (5) or derivatives thereof (6) can be converted directly to the azatetralone (11) using an alkyl lithium compound such as sec-, t-, or n-butyllithium, preferably t-butyllithium. The reaction is performed at a temperature of between about −78° C. to about −20° C., preferably −78° C. The acid (5) is believed to proceed through (9) and (10) to produce the azatetralone (11). The ester (6) where $R^6$ is —$OR^9$ and the amide (6) where $R^6$ is -$NR^7R^8$ are converted using the same procedure and are believed to proceed through (7) and (8) resulting in the azatetralone (11). The preferable method, however, is to use the amide (6) as the cycliacylation substrate.

The azatetralene (11) is then converted to the hydantoin aldose reductase inhibitor compound (12) by known methods (European Patent Application No. 86307712.1). These methods include condensing azatetralone (11) with an alkali metal cyanide (e.g., sodium cyanide or potassium cyanide) and ammonium carbonate to form the spiro-imidazolidinedione product having the formula (12). The reaction is typically carried out in the presence of a inert polar organic solvent including cyclic ethers such as dioxane and tetrahydrofuran, lower alkylene glycols like ethylene glycol, water miscible lower alkanols such as methanol, as well as N,N-di(lower alkyl) lower alkanoamides such as N,N-dimethylacetamide or formamide, preferably the latter. In general, this reaction is conducted at temperatures from about 25° C. to about 150° C. Upon completion of the reaction, the desired product is isolated in a conventional manner, by dilution with ice water and acidification. Further purification can be carried out by silica gel column chromatography.

The pharmaceutically acceptable acid addition salts of the final aldose reductase inhibitor compounds are prepared by treating the aforementioned organic bases with various mineral and organic acids which form non-toxic acid addition salts having pharmacologically acceptable anions, such as the hydrochloride, hydrobromide, hydroiodide, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts.

These compounds are all readily adapted to therapeutic use as aldose reductase inhibitors for the control of chronic diabetic complications, in view of their ability to reduce lens sorbitol levels in diabetic subjects to a statistically significant degree. The preferred compound, 6'-chloro-1',2',3',4'-tetrahydro-spiro-[imidazolidine-4,4'-quinoline]-2,5-dione, has been found to consistently control (i.e., inhibit), the formation of sorbitol levels in diabetic rats to a significantly high degree when given by the oral route of administration at dose levels ranging from 0.25 mg/kg to 25 mg/kg., respectively, without showing any substantial signs of toxic side effects. In general, these compounds are ordinarily administered using dosage forms at concentration levels ranging from about 0.5% to about 90% by weight of the total composition, in dosages ranging from about 0.25 mg to about 25 mg per kg of body weight per day, depending upon the weight and condition of the subject being treated and the particular route of administration chosen.

The aldose reductase inhibitor compounds may be administered either alone or in combination with pharmaceutically acceptable carriers for either oral or parenteral administration using single or multiple dosages. These forms of administration include tablets, capsules, losenges, troches, hard candies, powders, sprays, aqueous suspensions, injectable solutions, elixirs, syrups, and the like. Such carriers include solid diluents or fillers, sterile aqueous media and various non-toxic organic solvents, etc.

For purposes of oral administration, tablets containing various excipients such as sodium citrate, calcium carbonate and calcium phosphate may be employed along with various disintegrants such as starch, preferably potato or tapioca starch, alginic acid, and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter dyes, and if so desired, emulsifying and/or suspending agents as well, together with such diluents as water, ethanol, propylene glycol, glycerin and various like combinations thereof.

For purposes of parenteral administration, solutions of these compounds in sesame or peanut oil or in aqueous propylene glycol may be employed. It is also possible to administer these compounds topically using an appropriate opthalmic suspension suitable for the present purposes at hand, which can be given dropwise to the eye.

EXAMPLE 1

2,3-dibromo-5-chloropyridine (2)

3-bromo-5-chloropyridone (33.51 g, 161 mmol) was dissolved in dimethylformamide (251 ml) at ambient temperature. Phosphorus (V) tribromide oxide (52.12 g, 182 mmol) was added and the reaction heated to 80° C. for 72 hours. After cooling, the reaction was poured onto ice. Vacuum filtration provided the product as a tan solid. The crude product was taken up in ether and the pH of the water layer was adjusted to 13 with aqueous sodium hydroxide. The aqueous layer was extracted three times with ether, the combined organic extracts treated with magnesium sulfate, and the solvent removed under vacuum. The product was dissolved in boiling hexane and decolorizing carbon was added to the crude product, the contents heated to reflux and then filtered through celite. The clear colorless filtrate was tripped under vacuum to yield the title compound as a white solid (18.1 g, 45%), mp=39.5°–43° C. The starting pyridone was recovered from the aqueous layer of the ether extraction by adjusting the pH to 1 with concentrated hydrochloric acid. Filtration of the precipitate and drying in a vacuum provided 13.8 g (40%) of the starting pyridone. IR(neat): 3060, 1538, 1405, 1370, 1135, 1030, 905 cm$^{-1}$. $^1$H NMR Bruker 250 MHZ (CDCl$_3$)δ: 8.28 (d, J=2 Hz); 7.89 (d, J=2 Hz). $^{13}$C NMR (CDCl$_3$)δ: 146.93, 141.45, 141.02, 131.34, 124.01. Combustion analysis calculated for C$_5$H$_2$Br$_2$ClN: C, 22.13; H, 0.74; N, 5.16. Found: C, 21.93; H, 0.53; N, 4.90.

EXAMPLE 2

3-Bromo-5-chloro-2-[[(tetrahydro-2H-pyran,2-yl)oxy]butyl]-pyridine (3)

To form the Grignard reagent magnesium, bromo-4-[(tetrahydro-2H-pyran-2yl) oxy]butyl a suspension of magnesium turnings (470 mg, 19.4 mmol) in 15 ml of dry tetrahydrofuran (THF) was added a single crystal of iodine. To this mixture under argon was added 0.60 ml (3.2 mmol) of 4-bromo[(tetrahydro-2H-pyran-2yl)oxy]butane. The mixture was stirred and heated until reaction was initiated, at which time the remaining bromide (3.0 ml, 16.1 mmol) was added dropwise over a period of 5 minutes while the reaction temperature was maintained at a temperature of 45° C.

To a solution of the compound of Example 1 (2.0 g, 7.38 mmol) in tetrahydrofuran (7.4 ml) at ambient temperature is added 0.4 g (0.74 mmol) of 1,3-bis (diphenylphosphino)-propane nickel (11) chloride (dppp). The solution was cooled to 0° C. and 11 ml of the above Grignard reagent, was added over 30 minutes. Five minutes after the addition of the Grignard reagent, the reaction was quenched with 50 ml of water and 50 ml of saturated aqueous ammonium chloride. The quenched reaction was extracted twice with 50 ml of ether and the organic extracts combined and dried with magnesium sulfate. Removal of the solvent under vacuum provided 3.48 g of crude product. Chromatography on 80 g of silica with 10% ethyl acetate in hexane gave 2.04 g (79%) the title compound as a colorless oil. IR(neat): 3060, 2940, 2880, 1380, 1120, 1040 cm$^{-1}$. $^1$H NMR Bruker 250 MHz (CDCl$_3$)δ: 8.4(d, J=2.5 Hz, 1 H); 7.83 (d, J=2.5 Hz, 1 H); 4.56 (t, J=2.5 Hz, 1 H); 3.75 (m, 2 H), 3.40 (m, 2 H); 2.95 (t, J=12 Hz, 2 H); 1.67 (m, 10H). $^{13}$C NMR (CDCl$_3$)δ: 158.7, 146.6, 139.3, 129.3, 120.8, 98.8, 67.2, 62.2, 36.6, 30.8, 29.4, 25.5, 25.0, 19.6. Combustion analysis calculated for C$_{14}$H$_{19}$BrClNO$_2$: C, 48.22; H, 5.49; N, 4.02. Found: C, 48.52; H, 5.42; N, 4.02. Low resolution mass spectrum: m/e=248 (p).

EXAMPLE 3

3-Bromo-5-chloro-2-(butan-4-ol)-pyridine (4)

A solution of the compound of Example 2 (2.0 g, 5.74 mmol) in ethanol (53 ml) was treated with 148 mg (0.59 mmol) pyridinum p-toluenesulfonate (ppts) and the solution heated to 55° C. for 5.5 hours. The solvent was removed under vacuum, and the colorless oil remaining was chromatographed on silica (60 g) with 35% ethyl acetate in hexane to afford 1.466 g, (97%) of the title compound as a white solid. mp=55°-56° C. IR (nujol mull): 3160, 1380, 1040 cm$^{-1}$. $^1$H NMR (CDCl$_3$)δ: 8.35 (d, J=2 Hz, 1 H); 7.80 (d, J=2 Hz, 1 H); 3.65 (t, J=10 Hz, 2 H); 2.97 (s, 1 H); 2.90 (t, J=10 Hz, 2 H); 1.71 (m, 4H). $^{13}$C NMR (CDCl$_3$)δ: 158.6, 146.4, 139.5, 129.5, 121.0, 62.2, 36.2, 32.1, 24.4. Combustion analysis calculated for C$_9$H$_{11}$BrClNO: C, 40.86; H, 4.19; N, 5.29. Found C, 41.02; H, 4.15; N, 5.14.

EXAMPLE 4

3-Bromo-5-chloro-2-(4-butanoic acid)-pyridine (5)

A solution of the compound of Example 3 (8.8 g, 33.3 mmol) in acetone (98 ml) at 0° C. was treated dropwise with 21 ml (56.2 mmol) of Jones reagent over 30 minutes. Upon completion of the addition, the reaction was stirred for 30 minutes at 0° C. 20 ml of isopropanol was then added, the temperature adjusted to 5° C., and the reaction stirred for 15 minutes. The dark green solids were filtered off and washed with 100 ml of isopropanol. The solvent was removed under vacuum yielding a paste. This residue was treated with 100 ml of ethyl acetate and 100 ml of water. The phases were separated and the organic phase extracted three times with aqueous saturated sodium bicarbonate (75 ml each). The basic aqueous extracts were acidified to pH 2 with 6N HCl, and extracted twice with ethyl acetate (100 ml each). The organic extracts were dried with magnesium sulfate, and the solvent removed under vacuum affording the title compound (6) as an oil which solidified to a white solid on standing (5.69 g, 61%). mp=87°-89° C. IR (nujol mull): 3050, 1710, 1575, 1280 cm$^{-1}$. $^1$H NMR (CDCl$_3$)δ: 10.5 (bs, 1 H); 8.44 (d, J=2.5 Hz, 1 H); 7.83 (d, J=2.5Hz, 1 h); 2.98 (t, J=7Hz, 2 H); 245 (t, J=7. Hz, 2 H); 2.05 (dd, J=7 Hz, J=7 Hz, 2 H). $^{13}$C NMR (CDCl$_3$)δ: 178.5, 157.6, 145.4, 139.8, 129.9, 121.1,35.6, 33.3, 23.1. Combustion analysis calculated for C$_9$H$_9$BrClNO$_2$: C, 38.81; H, 3.26; N, 5.03. Found: C, 38.77; H, 3.23; N, 5.00.

EXAMPLE 5

3-Bromo-5-chloro-2-(4-N,N' dimethylbutamide)-pyridine (6)

Dimethylamine gas was bubbled through a solution of the compound of Example 4 (200 mg, 0.719 mmol) and 1-3-dimethylaminopropyl)-3-ethylcarbodiimide hydrochloride ([DECD], 106 mg, 0.836 mmol) in 20 ml methylene chloride at ambient temperature for 30 minutes. 15 ml of water, 15 ml of 4N aqueous HCl and 10 ml of saturated aqueous sodium chloride were added to the reaction. The organic phase was separated, treated with magnesium sulfate, and the solvent removed under vacuum to yield 137 mg (62%) of the title compound as an oil. IR(neat): 3420, 2940, 1640, 1430, 1050 cm$^{-1}$. $^1$H NMR (CDCl$_3$)δ: 8.42 (d, J=2.5 Hz, 1 H); 7.82 (d, J=2.5 Hz, 1 H); 3.01 (s, 3 H); 3.00 (t, J=8 Hz, 2 H); 2.94 (s, 3 H); 2.40 (t, J=8 Hz, 2 H); 2.08 (dd, J=7 Hz, J=7 Hz, 2 H). $^{13}$C NMR (CDCl$_3$ 67 : 172.5, 158.2, 146.5, 139.4, 129.5, 121.1, 36.2, 35.4, 32.6, 29.7, 23.5. Low resolution mass spectrum: m/e=304(p).

EXAMPLE 6

3-Chloro-7,8-dihydro-5(6H)-quinolone (11 )

The compound of Example 5 (50 mg, 0.164 mmol) in 2.0 ml of diisopropylether was cooled to –70° C. 150 microliters (0.255 mmol) of t-butyllithium was added. The reaction was stirred for 45 minutes and then quenched with 2N HCl. 10 ml of water and 10 ml of diisopropylether were added and the phases separated. The aqueous phase was again extracted twice with diisopropylether (210 ml each). The combined organic extracts were treated with sodium sulfate, and the solvent removed under vacuum affording 24 mg of an amber oil. The oil was chromatographed on silica with 30% ethyl acetate in hexane yielding 15.5 mg, (50%) of the title compound as white needles. mp=84°-86° C. IR (nujol): 2960, 2930, 2860, 1690, 1572, 1540, 1469, 1385, 1290, 1050, 990 cm$^{-1}$. $^1$H NMR (CDCl$_3$)δ: 8.58 (d, J=2.5 Hz, 1 H); 8.18 (d, J=2.5 Hz, 1 H); 3.10 (t, J=10 Hz, 2 H); 2.65 (t, J=10 Hz, 2 H); 2.16 (m, 2 H). $^{13}$C NMR (CDCl$_3$) δ: 196.6, 161.4, 152.2, 134.1, 130.8, 128.7, 38.2, 32.0, 21.7. High resolution mass spectrum: m/e=183.022 (calculated for C$_9$H$_9$ClNO m/e=183.265).

EXAMPLE 7

3-Bromo-5-chloro-2-[(2S)-methyl-4-[(tetrahydro-2H-pyran-2-yl)oxy]buty]-pyridine (3)

The Grignard reagent magnesium, bromo [2-(R)-methyl-4-[(tetrahydro-2H-pyran-2yl)oxyl]butyl] was formed by adding magnesium (1.22 g) under nitrogen to THF (38.8 ml) followed by one crystal of iodine. Approximately 2. ml of 2-(R)-methyl-4-[(tetrahydro-2H-pyran-2yl)oxy]butane (12.5 g total added) was added. The Grignard reaction was initiated after approximately 10 minutes at ambient temperature. The remaining bromide was added dropwise over 15 minutes. After the reaction was complete, the Grignard reagent was stirred at between 40° and 45° C. for 1 hour. 2,3-dibromo-5-chloro-pyridine (5.7 g), THF (21 ml), and dppp (1.14 g) were reacted with the above Grignard reagent in a flame dried flask. The reddish brown suspension was cooled to 0° C. and the Grignard reagent added dropwise over 1 hour. TLC showed a faint trace of starting material after all the Grignard reagent was added. The reaction was inverse quenched into water (140 ml), aqueous saturated ammonium chloride (140 ml), and diethyl ether (280 ml). The phases were separated and the aqueous phase again extracted with ether (280 ml). The combined organic phases were dried with magnesium sulfate, and solvents removed under vacuum to afford an amber oil (14.2 g). Chromatography of the oil on 228 g of silica eluting with 10% ethyl acetate in hexane afforded a light yellow oil (4.97 g, 65%). IR(CHCl$_3$): 2931, 2865, 1453, 1440, 1430, 1373, 1355, 1354, 1185, 1117, 1071, 1020, 975 cm$^{-1}$. Low resolution mass spectrum: m/e=85 (base peak). [α]$_D$=+1.32°(c=1.06 EtOH).

EXAMPLE 8

3-Bromo-5-chloro-2-(butan-(2S),methyl-4-ol)pyridine (4)

4.78 g of the title compound of Example 7 was dissolved in ethanol (128 ml) and ppts (0.353 g) was added. This solution was heated to 55° C. for 4 hours and TLC showed the reaction complete. After 4.5 hours reaction time, the solution was cooled and the solvent removed under vacuum to afford a yellow oil (4.76 g). Chromatography on silica eluting with 35% ethyl acetate in hexane yielded a colorless oil (3.09 g, 84%). IR (CHCl$_3$) 3606, 3396, 2949, 2926, 2874, 1566, 1428, 1374, 1191, 1033, 997 cm$^{-1}$. $^1$H NMR (CDCl$_3$) δ: 8.42 (d, J=2, 1H); 7.85 (d, J=2, 1H); 3.72 (m, 2 H); 2.89 (dd, J=6, J=7, 2H); 2.23 (dd, J=6, J=7, 1H); 2.09 (m, 1 H); 1.59 (m, 2 H); 0.97 (d, J=7, 3H). $^{13}$C NMR (CDCl$_3$) 67 : 157.8, 146.2, 139.7, 129.5, 121.6, 60.6, 43.2, 39.3, 29.7, 19.9. Low resolution mass spectrum: m/e=280(p). [α]$_D$=−2.29(C=1.04, acetone).

EXAMPLE 9

3-Bromo-5-chloro-2-(butan-(2S) methyl-4-butanoic acid)-pyridine (5)

The title compound of Example 8 (1.05 g) was dissolved in acetone (20 ml) and cooled to 0° C. Jones reagent (7.5 ml) was added over 5 minutes, the reaction was stirred 3.5 hours, and then quenched with isopropanol (30 ml). After stirring for 20 minutes, the acetone was stripped under vacuum. Water (40 ml) and ether (100 ml) were added, the phases were separated and the aqueous layer was extracted again with ether (100 ml). Water (40 ml) was added to the combined organic layers and aqueous sodium hydroxide was added (15% aqueous NaOH, 1.2 ml) to adjust the pH to 12, at which time the organic layer was removed. Ether (50 ml) was added to the basic aqueous solution and aqueous HCl (1N, 4.0 ml) added to adjust the pH to 2. The phases were separated and the aqueous layer extracted twice with ether (2×50 ml). The combined organic layers were dried with magnesium sulfate and the solvent removed under vacuum to yield the acid as a colorless oil (755 mg, 68%) which solidified on standing, mp=59°–60° C. IR (CHCl$_3$): 3496, 2958, 1711, 1565, 1513, 1429, 1374, 1271, 1193, 1119, 1033 cm$^{-1}$. $^1$H NMR (CDCl$_3$ δ: 8.45 (d, J=2 Hz, 1 H); 7.88 (d, J=2 Hz, 1 H); 2.96 (d, J=7 Hz, 2 H); 2.55 (m, 1 H); 2.35 (m, 2 H); 1.05 (d, J=7 Hz, 3 H). $^{13}$C NMR (CDCl$_3$) δ: 178.0, 156.9, 146.3, 139.8, 129.9, 121.7, 42.6, 40.7, 30.0, 19.8. Low resolution mass spectrum: m/e=291 (p).

EXAMPLE 10

3-Bromo-5-chloro-2-(butan-(2S) methyl-4-N,N' dimethylbutamide)-pyridine (6)

To a solution of the title compound of Example 9 (430 mg) in methylene chloride (10.3 ml) was added 1-(3-dimethyl-aminopropyl)-3-ethylcarbodiimide HCl (340 mg). Dimethylamine gas was bubbled into the solution for 1 hour at ambient temperature. The resulting solution was stirred for 2 hours, after which water (20 ml) was added, the phases were separated, and the organic phase dried with magnesium sulfate. Upon removal of the solvent under vacuum a pale yellow oil (240 mg) was obtained. Chromatography on silica (6 g) eluting with 90% ethyl acetate in hexane gave the product as a colorless oil (190 mg, 41%). IR (CHCl$_3$): 3419, 2958, 2879, 1632, 1565, 1495, 1440, 1427, 1400, 1373, 1350, 1195, 1117, 1055, 1032 cm$^{-1}$. $^1$H NMR (CDCl$_3$) δ: 8.38 (d, J=2 Hz, 1 H); 7.80 (d, J=2 Hz, 1 H); 2.95 (s, 3 H); 2.87 (m, 2 H): 2.86 (s,3 H); 2.61 (dq, J=7 Hz, 1 H); 2.29 (dd, J=6 Hz, J=7 Hz, 2 H); 0.98 (d, J=7 Hz, 3 H). $^{13}$C NMR (CDCl$_3$) δ: 171.9, 157.5, 146.3, 139.4, 129.5, 121.5, 43.6, 39.9, 37.4, 35.4, 29.9, 20.2. Low resolution mass spectrum: m/e=319 (p).

EXAMPLE 11

3-Chloro-7,8-dihydro-(7S)-methyl-5(6H)-quinolinone (11)

t-Butyllithium (1.7M, 0.130 ml) was added to the title compound of Example 10 (45 mg) in isopropyl ether (1.4 ml) at −78° C. The reaction was stirred for 15 minutes and then was quenched with aqueous saturated ammonium chloride (3 ml). The quenched solution was extracted with ether and the organic phase dried to afford a pale yellow oil (48 mg). Chromatography on silica (800 mg) eluting with 25% ethyl acetate in hexane gave a white solid (15.4 mg, 57%). mp=50°–52° C. IR (CHCl$_3$): 2953, 1693, 1578, 1555, 1445, 1382, 1348, 1271, 1203, 1159, 907 cm$^{-1}$. $^1$H NMR (CDCl$_3$) δ: 8.62 (d, J=2.5 Hz, 1 H); 8.20 (d, J=2.5 Hz, 1 H); 3.11 (m, 1 H); 2.77 (m, 2 H); 2.38 (m, 2 H); 1.15 (d, J=6 Hz, 3 H). $^{13}$C NMR (CDCl$_3$) δ: 196.9, 160.8, 152.4, 134.1, 130.8, 128.2, 46.3, 40.2, 29.2, 21.2. High resolution mass spectrum: m/e=195.04434 (calcd. for C$_{10}$H$_{10}$ClNO 195.0449). [α]$_D$=+27° (c=0.8 CDCl$_3$).

I claim:

1. A process for preparing a compound of the formula

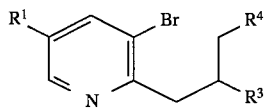

wherein R$^1$ is hydrogen, fluoro, chloro, bromo, nitro, trifluoromethyl, C$_1$ to C$_4$ alkoxy, C$_1$ to C$_4$ alkylthio or C$_1$ to C$_6$ alkyl, R$^3$ is hydrogen or C$_1$ to C$_6$ alkyl, R$^4$ is —CH$_1$=CH$_2$ or —CH$_2$-YR$^5$, Y is oxygen or sulfur, and R$^5$ is an acid labile alcohol protecting group comprising reacting a compound of the formula

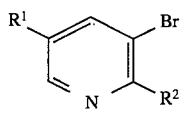

wherein R$^2$ is bromo or iodo and R$^1$ is as defined above with a Grignard reagent of the formula

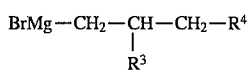

wherein R$^3$ and R$^4$ are as defined above in the presence of a phosphine ligand catalyst and at a sufficiently low temperature such that a regiospecific displacement of only the R$^2$ substitutent occurs.

2. The process of claim 1 wherein said temperature is between about −20° and about 15° C.

3. The process of claim 1, wherein said phosphine liguand catalyst is 1,3-bis(diphenylphosphino)ethane nickel (II) chloride (dppp).

* * * * *